United States Patent [19]

Hamelin et al.

[11] Patent Number: 5,565,771
[45] Date of Patent: Oct. 15, 1996

[54] APPARATUS FOR INCREASING LINEAR RESOLUTION OF ELECTROMAGNETIC WIRE ROPE TESTING

[75] Inventors: Michel Hamelin, St-Lazare; Frank Kitzinger, Montreal, both of Canada

[73] Assignee: Noranda, Inc., Toronto, Canada

[21] Appl. No.: 374,101

[22] Filed: Jan. 18, 1995

[51] Int. Cl.$^6$ ............................ G01R 33/12; G01N 27/72
[52] U.S. Cl. ........................ 324/225; 324/227; 324/235; 324/242
[58] Field of Search ................................. 324/225, 235, 324/240, 241, 242, 243, 227, 239, 226

[56] References Cited

U.S. PATENT DOCUMENTS

| | | | |
|---|---|---|---|
| 4,096,437 | 6/1978 | Kitzinger et al. | 324/227 |
| 4,210,866 | 7/1980 | Paulson | 324/225 |
| 4,495,465 | 1/1985 | Tomaiuolo et al. | 324/232 |
| 5,036,277 | 7/1991 | van der Walt | 324/235 |

OTHER PUBLICATIONS

Weischedel, "In-service inspection of wire ropes: state of the art", Mining Science & Technology, 1990, 11, 85–93.
Kuun et al. "Condition assessment of winding ropes", presented at the 2nd International Conference on Mine Hoisting, London, England, Jun. 28–30, 1993.

*Primary Examiner*—Walter E. Snow
*Attorney, Agent, or Firm*—Fitzpatrick, Cella, Harper & Scinto

[57] ABSTRACT

A magnetic testing device for detecting loss of metallic area and internal and external defects in elongated magnetically-permeable objects includes a permanent magnet assembly having poles adapted to be spaced apart in the longitudinal direction of an elongated object for inducing a longitudinal magnetic flux in a section of the object between the poles of the magnet assembly, the magnet assembly being strong enough to magnetically saturate the section of the object. A tubular pole piece is arranged to surround the object adjacent each pole of the permanent magnetic assembly for directing the magnetic flux into the object at one pole and out of the object at the other pole. Hall effect devices are placed in the path of the magnetic flux for sensing the reduction of the flux passing through the elongated object due to any reduction of cross-sectional area of the elongated object between the pole pieces caused by loss of metallic area in the elongated object. A leakage flux sensor is installed between the pole pieces for detecting an external and internal defects in the objects. Circuitry is provided for increasing the linear resolution of the metallic area measurement of the object, whereby signals obtained correspond more closely to the variations in the metallic area of the elongated object. Preferably, the circuitry combines the local fault (LF) signal with the loss of metallic area (LMA) signal to benefit from both the high linear resolution of the LF signal and the long range stability of the LMA signal to improve the resolution of the LMA signal.

9 Claims, 5 Drawing Sheets

APPARATUS FOR INCREASING LINEAR RESOLUTION OF ELECTROMAGNETIC WIRE ROPE TESTING

FIELD OF INVENTION

The present invention is concerned with an improvement to current nondestructive wire rope testing devices.

BACKGROUND OF THE INVENTION

Many non-destructive testers for elongated objects such as wire ropes are presently available. Most of these testers comprise electromagnets or permanent magnets which induce a magnetic flux in the objects, and include means for detecting leakage of the flux from these objects. Typically, flux leakages are caused by two different phenomena, namely (a) internal or external defects, also called "local faults", and (b) loss of metallic area due to wear, rust and the like. The former cause of flux leakage is generally localized, while the latter is not.

Current testers operate in the following manner: the elongated object is passed through the tester which is equipped with sensors located between the poles of the magnet, the sensors being adapted to detect flux leakages caused by internal and/or external defects, and by loss of metallic area. Two signals, namely the local fault signal (LF) and loss of metallic area signal (LMA), are therefore generated. An example of such tester is disclosed and claimed in U.S. Pat. No. 4,096,437, which is hereby incorporated by reference.

Problems encountered with current testers are that each signal must be interpreted according to the physical characteristics of the sensing head. Furthermore, the LF signal only serves qualitative purposes because it varies with the spatial derivative of the leakage flux as measured by the LF sensors.

Those problems are summarized by Kuun et al. in "Condition assessment of Winding Ropes" in the Proceedings of the $2^{nd}$ International Mine Hoisting Conference in London, UK, Jun. 28–30, 1993, paper 6.2, particularly in page 6.2.2, $2^{nd}$ column, $5^{th}$ paragraph wherein it is stated that "Existing EM (electromagnetic) instruments do not provide a true indication of steel area at a given cross-section of the rope. Area output is a mean value over a rope length varying from 50 to 360 mm.( . . . ) Finally, EM output is not an absolute value but merely a variation relative to the area of the rope at the location where the output was last set to zero".

Accordingly, even though valuable information is provided with testers presently in use, there is a great need to improve their efficiency in terms of the indication of steel area at a given cross-section of the rope.

SUMMARY OF THE INVENTION

In accordance with the present invention, there is now provided an improvement to current electromagnetic testers for detecting loss of metallic area and internal and external defects in elongated magnetically permeable objects. More specifically, the improvement comprises the addition to the tester of means using the signal generated by an internal and external defect sensor (local fault or LF signal), in combination with the signal generated by a loss-of-metallic-area sensor (LMA signal), in order to convert the latter in a signal corresponding more closely to the variations in the metallic area of the object.

The means for achieving the above improvement is preferably a digital signal processing unit containing a data acquisition system and a digital signal processor, the unit being adapted to use the LF signal and the LMA signal, and to generate a higher linear resolution LMA signal, thus allowing one to locate precisely the location and extent of and defect in the elongated object.

More preferably, the digital signal processing unit comprises one or more filters to reduce or suppress the long range drift of the local fault signal and/or the noise of the metallic area signal.

DETAILED DESCRIPTION OF THE INVENTION

The improvement disclosed in the present application relates to the increase of the linear resolution of the metallic area measurement of an object, preferably a wire rope, whereby signals obtained correspond more closely to the variations in the metallic area of the elongated object. It was made possible by the recent availability of computerized wire rope testing instruments. The implementation of this improvement is presented in the context of an upgrading of a wire rope tester such as that disclosed and claimed in U.S. Pat. No. 4,096,437. The tester disclosed in the latter patent, commercially available under the trademark MAGNOGRAPH™, as most of the other commonly used instruments in the field of Non Destructive Testing (NDT) of wire ropes, provides two important informations: a loss of metallic area signal and a local fault signal. The unique features of the MAGNOGRAPH™ come from the physical measurement principle used in the sensor head. This principle, the Hall effect, makes possible magnetic flux density measurements in a magnetization circuit for both steady state and dynamic operation.

For the purpose of exemplifying the beneficial effects of the present invention, the MAGNOGRAPH™ has been used as the non-destructive testing instrument in the specification. Those skilled in the art will, however appreciate that the present improvement may be applied to other testers generating signals similar to those mentioned above, that is, signals generated from direct measurement of the magnetic flux density in LMA and LF measurement circuits.

Figure 1:
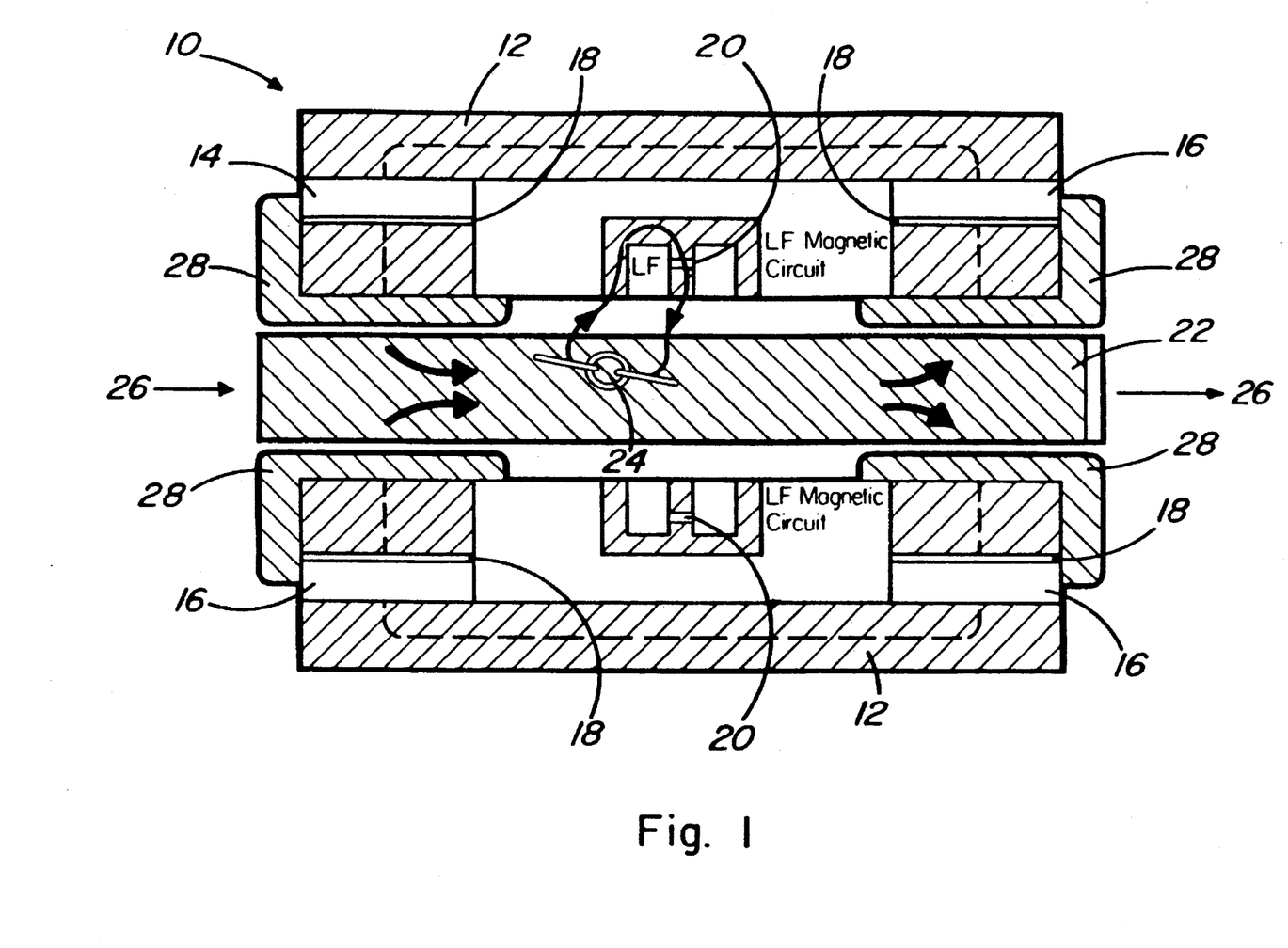
FIG. 1 is a schematic diagram of the wire rope tester disclosed and claimed in U.S. Pat. No. 4,096,437.

Referring to FIG. 1, there is illustrated a schematic diagram of the tester MAGNOGRAPH™ 10, which comprises U-shaped magnets 12 having a north pole 14 and a south pole 16. Loss of metallic area sensors 18 are placed at the end of poles 14 and 16. Local fault sensors (or Hall sensors) 20 are positioned between poles 14 and 16 of each magnet 12. In operation, a wire rope 22 comprising one or more defects 24 is advanced into tester 10 in the direction indicated by arrows 26. Tester 10 further comprises guides 28 to facilitate the passage of wire rope 22 therein. It should be noted that defects 24 can be either on the surface or inside wire rope 22.

Computerized instrument

Figure 2:
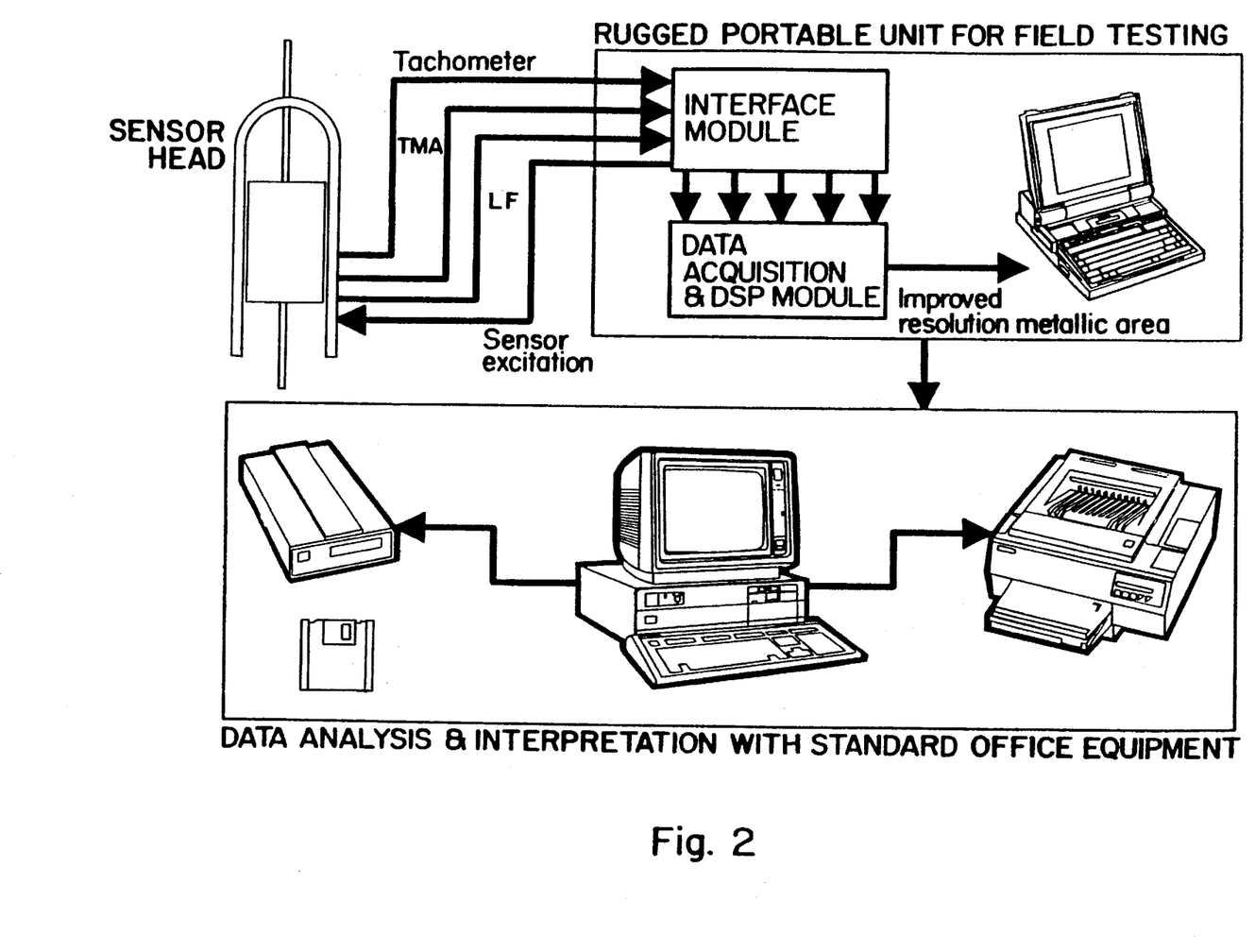
FIG. 2 is a schematic diagram of the present improved electromagnetic testing instrument.

Complex signal processing is best performed with digital systems. For this reason, the operator console of tester 10 comprising the present improvement is computerbased. Referring to FIG. 2, the console, which includes a data acquisition system and a digital signal processor (DSP) module, is used for all aspects of data storage, presentation and analysis. The system uses pre-loaded calibration curves that relate output voltage from the Hall sensors 20 to total metallic area for various rope constructions. It is thus possible to compare the metallic area value from a cable under test to the metallic area of a new cable.

The computerized console is used for the automation of all the set-up and calibration steps prior to rope testing, and significantly reduces the risk of errors from the operator. It further improves the practical aspects of data inspection and analysis. This is especially the case for microprocessor-based Digital Signal Processing (DSP) that provides broader capabilities than currently used analog methods.

In a typical embodiment, the hardware used in the improved console is built around two main functional sections: first, a data acquisition section including a 12 bit resolution A/D converter with a 235,000 samples/second maximum sampling rate, an intel 80C186 processor, and a Motorola DSP56001 Digital Signal Processor with a clock speed of 20 MHz. This section is responsible for preliminary processing of the input signals, filtering and especially the execution of the algorithm described below and illustrated in FIG. 5. Four analog data channels are used: Total Metallic Area, Local Fault, temperature, and cable direction. An optical encoder, that was originally part of the instrument, is used to trigger one sample for every 4 mm of cable length. The incoming flow of data can be processed in real-time, or stored to be processed later.

A second section built around an intel 486DX2/66 microprocessor handles the data presentation and off-line processing, that is, scaling and zooming. This section also includes the drivers for a SVGA flat panel monitor, a keyboard and a floppy disk drive. The complete unit is preferably enclosed in a rugged case and can be operated either from 110 Vac power line or a set of rechargeable batteries by the use of a power inverter. It is understood that, as higher performance components become available, different hardware can be used to perform the same functions.

Digital Signal Processing

An original algorithm has been developed to process the signals generated from both the metallic area and local fault sensors. The processing described in this section may advantageously be performed in real time by the digital signal processing unit.

Two main detection principles have been used in the literature to measure loss- of-metal and to detect local faults in wire ropes. In each of them, the wire rope under test is placed in a magnetizing circuit in order to be brought to the magnetic saturation level.

In the first system, inductive coils are used to detect the variations of magnetic flux in and around the cable, i.e., the loss of metallic area. These variations are related to changes in the metallic cross-section of the cable, i.e. the defects. Due to the small length of the coils, these sensors will provide a signal related to a short portion of the cable. This feature, sometimes referred to as high quantitative or linear resolution, is claimed to be particularly valuable by manufacturers of coil based instruments.

The alternative to inductive coils are direct magnetic field sensors such as Hall effect devices, to measure the absolute value of the flux in the magnetizing circuit and to detect the leakage flux around the cable caused by local faults. The signals produced by Hall sensors based instruments represent an average of the ferro-magnetic mass between the two poles of the main magnetic circuit instead of local variation of the metallic mass for coil based instruments. In the MAGNOGRAPH™, the distance between the poles was chosen to represent roughly one lay-length of a commonly used wire rope, a distance considered to be "low quantitative resolution" by those skilled in the art of coil based instruments.

Figure 5:
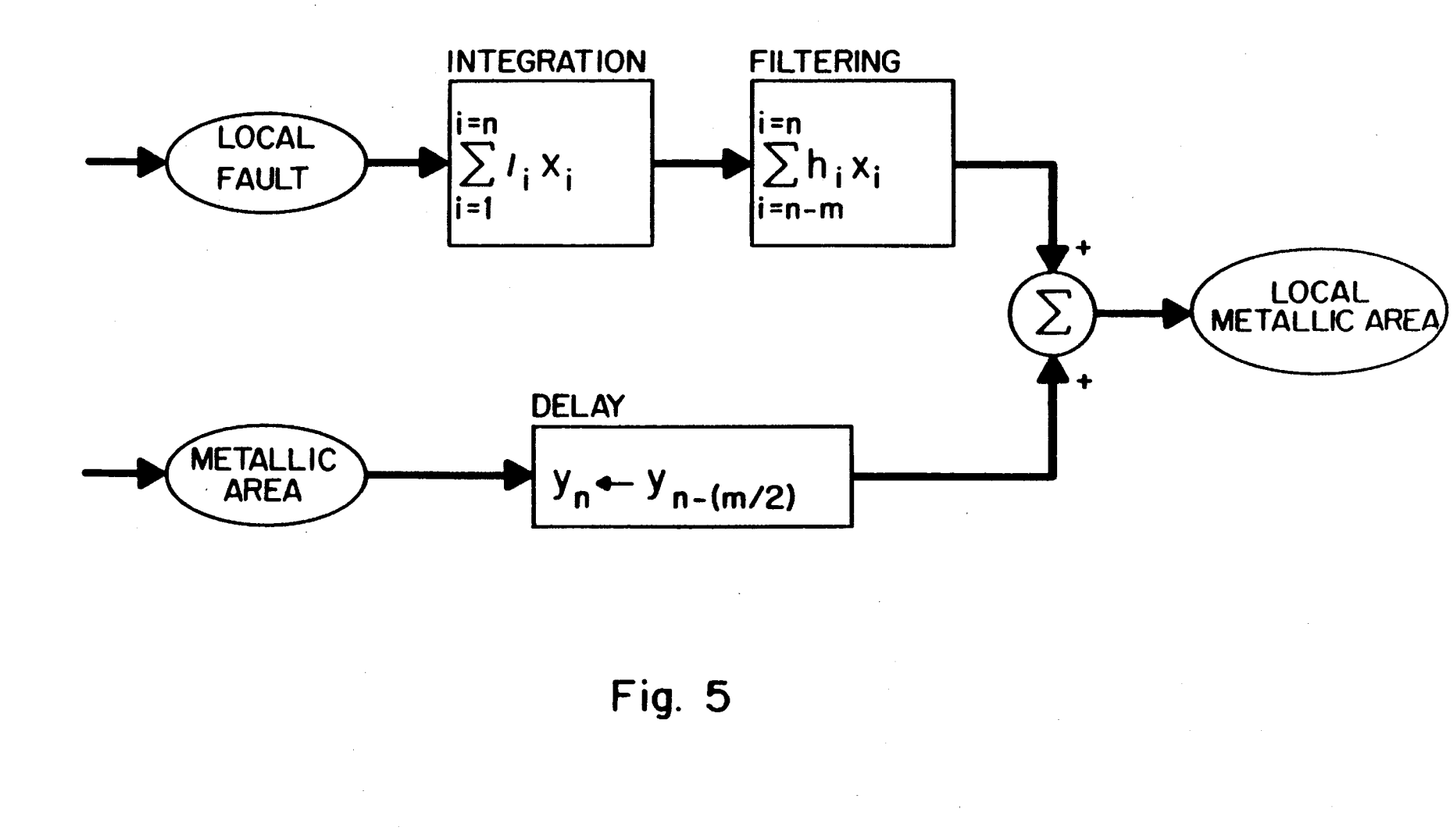
FIG. 5 illustrates the digital signal processing algorithm used to increase the linear resolution of the metallic area signal.

The improvement being the subject of this application allows the use of the LF signal generated by the localized leakage flux sensor of the MAGNOGRAPH™ to improve the linear (or quantitative) resolution of the metallic area signal, which can then be easily and readily analyzed by the operator. To reach that objective, both the short range variations of the local fault signal and the long range variations of the metallic area signal need to be exploited. To achieve this goal, the algorithm illustrated in FIG. 5 has been developed. The variables in the algorithm are as follows:

$x_i$ is the $i^{th}$ local fault measurement;

$y_n$ is the current metallic area measurement;

n is the number of samples corresponding to the measured length of wire rope;

m is the number of samples corresponding to the length of the sensor magnetic circuit;

$h_i$ is the FIR (Finite Impulse Response) filter coefficient; and $l_i$ is the length between samples.

The following operations are performed on the signals:

1) The LF signal is integrated to make it fluctuate in a similar manner as the LMA signal. It is important to eliminate any DC component from the LF signal prior to integration.

2) The modified LF signal is then filtered with a high pass filter specifically designed such that the response to a step input will correspond to the natural response of the sensor head. (i.e. when a step input is applied to this filter, the length over which the output is restored to zero equals the averaging length of the sensor head).

3) A delay corresponding to the distance between the LF sensor and the beginning of the avenging length of the sensor head is then applied to the modified LF signal in order for the latter to align itself properly with the LMA signal.

4) The modified LF signal is finally scaled and added to the LMA signal such that the resulting signal represents a higher linear resolution metallic area signal.

Because of its geometry, the local fault sensor generates a signal proportional to the rate of variation of the leakage flux produced by local variation of the metallic section, and should thus provide information similar to that of the inductive coil instruments. This allows one to process the local fault trace and to superimpose it on top of the signal given by the LMA sensor. It is thus possible to benefit from both the high linear resolution of the LF signal and the long range stability of the LMA signal to improve the resolution of the LMA signal.

Figure 3:
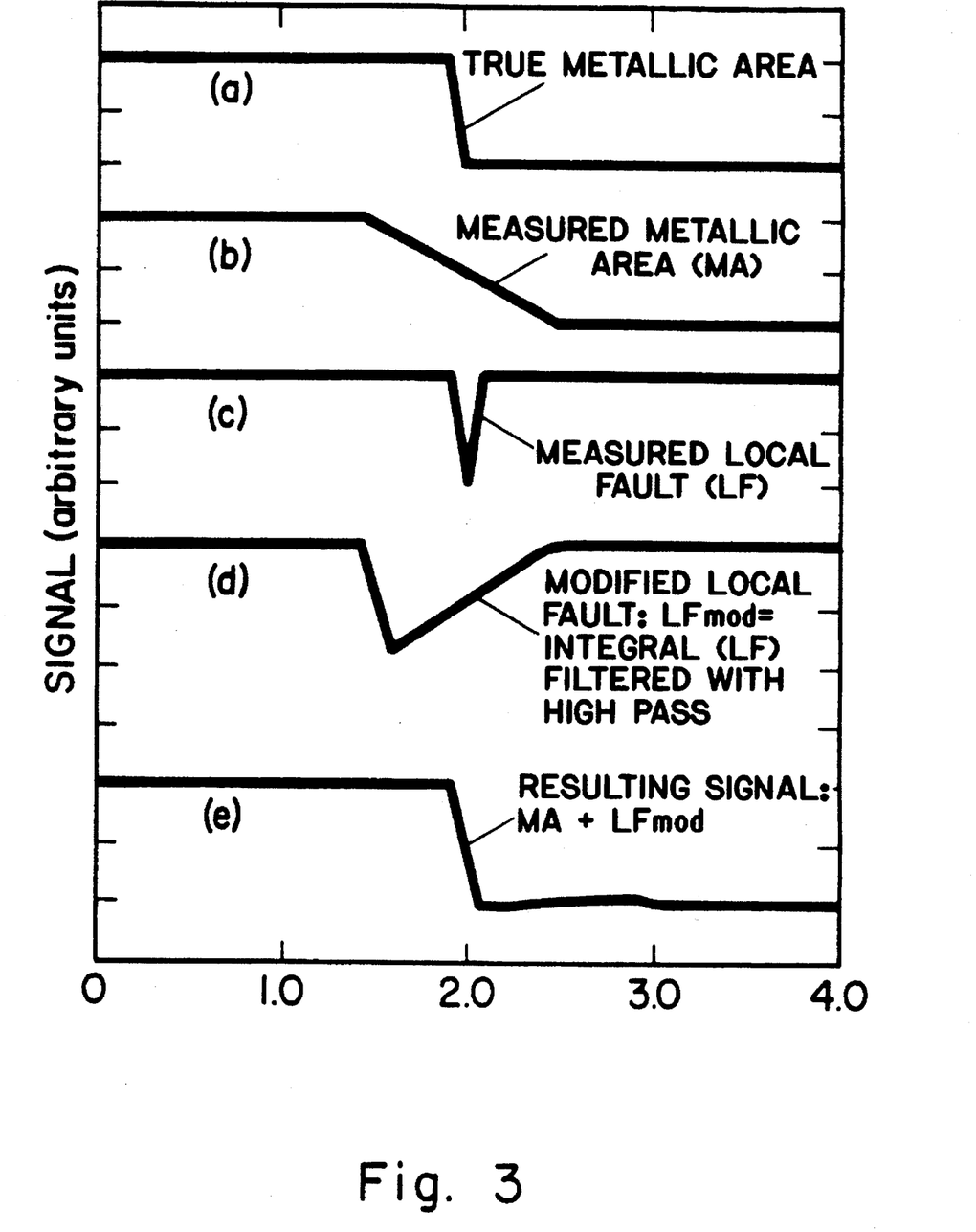
FIG. 3 illustrates the signals measured by an electromagnetic testing instrument in accordance with the present invention.

The signals generated from the sensors after each step of the processing in the digital signal processing unit (in the case of a step variation of the metallic area) are illustrated in FIG. 3. The first step is to apply a low pass filter on the metallic area signal and a high pass filter to the local hull signal (a). The LF signal is then integrated and filtered again with a proper high pass filter (b). These filters can be FIR (Finite Impulse Response) filters or any other conventional digital filter available. The use of digital filters, by opposition to analog filters is important since a delay has to be applied to the modified LF signal (c). The resulting modified LF signal is finally added to the LMA signal to obtain an improved linear resolution LMA signal (d).

FIR filters with 137 taps using the Hamming windowing technique are employed in the current realization of the invention. The local fault signal of wire rope testers such as the MAGNOGRAPH™ needs to be integrated because, as in the coil based instruments, this signal behaves like the spatial derivative of the metallic area of the rope under test (FIG. 3).

An important aspect of this processing is to choose a high pass filter for the integrated local fault signal with a response corresponding to the natural response of the sensor head. When the filter is properly chosen, the effect of a sudden change in metallic area will extend over the same length on the metallic area and integrated local fault signals (FIG. 3). The modified local fault signal needs then only to be shifted accordingly and added to the metallic area signal to obtain a local metallic area indication. This processing has the advantage of being insensitive to measurement noise since the integration of the local fault signal acts as low pass filter. A high spatial resolution metallic area signal is thus generated.

Figure 4:
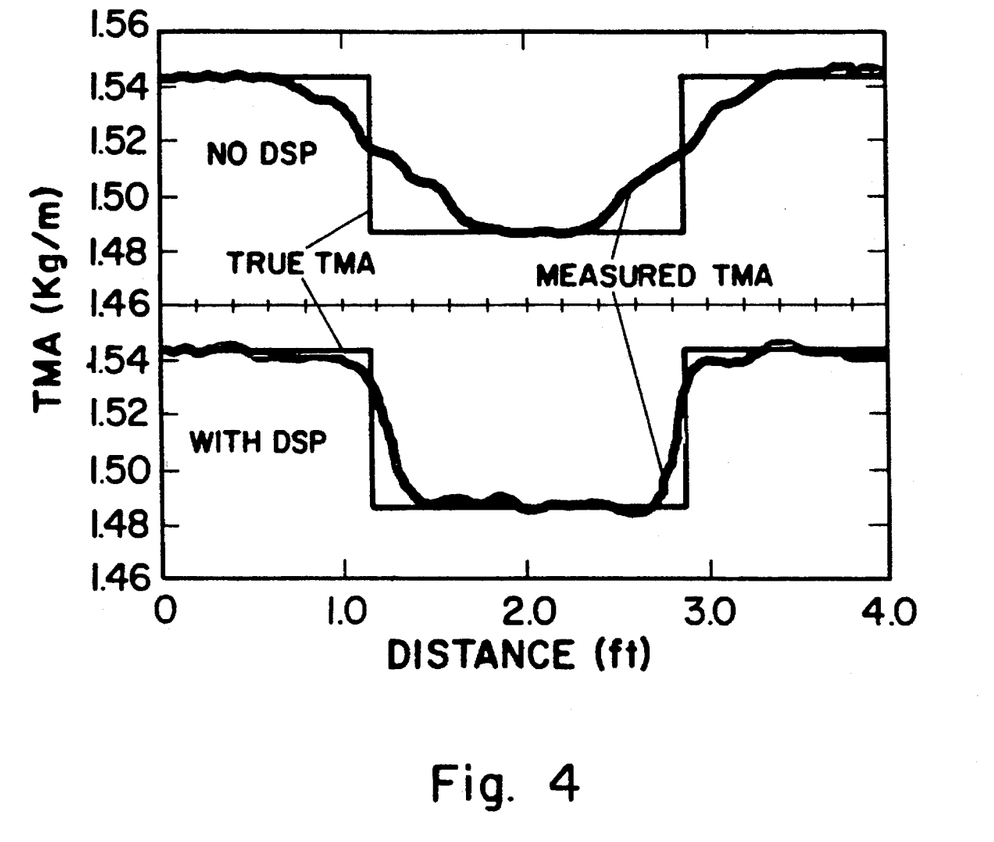
FIG. 4 is a comparison diagram between the signals obtained before and after the addition of the means combining the LF signal and the LMA signal.

FIG. 4 shows the improvement to the instrument output when the algorithm is applied to a sudden 3.7% loss of metal in a wire rope. This test was performed in the laboratory with a ¾" stranded rope.

While the invention has been described in connection with specific embodiments thereof, it will be understood that it is capable of further modifications and this application is intended to cover any variations, uses or adaptations of the invention following, in general, the principles of the invention and including such departures from the present disclosure as come within known or customary practice within the art to which the invention pertains, and as may be applied to the essential features hereinbefore set forth, and as follows in the scope of the appended claims.

What is claimed is:

1. A magnetic testing device for detecting loss of metallic area and internal and external defects in elongated magnetically permeable objects, the device comprising:

(a) a permanent magnet assembly having poles adapted to be spaced apart in the longitudinal direction of an elongated object for inducing a longitudinal magnetic flux in a section of the object between the poles of the magnet assembly, the magnet assembly being strong enough to magnetically saturate the section of the object;

(b) a tubular pole piece adapted to surround the object adjacent each pole of the permanent magnet assembly for directing the magnetic flux radially into the object at one pole and out of the object at the other pole;

(c) Hall effect devices placed in the path of the magnetic flux for sensing the reduction of the flux passing through the elongated object due to any reduction of cross sectional area of the elongated object between the pole pieces caused by loss of metallic area in the elongated object; and (d) a leakage flux sensor installed between the pole pieces for detecting external and internal defects in the objects; and (e) means for increasing the linear resolution of the metallic area measurement of the object, whereby signals obtained correspond more closely to the variations in the metallic area of the elongated object said means for increasing including means for transforming a leakage flux sensor signal into a trace that, added to a loss of metallic area signal, results in a high linear resolution metallic area measurement.

2. A magnetic testing device according to claim 1 wherein the means for increasing the linear resolution of the metallic area measurement is a digital signal processing unit.

3. A magnetic testing device according to claim 2 wherein the processing unit comprises a data acquisition system and a digital signal processor.

4. A magnetic testing device according to claim 3 wherein the digital signal processor comprises at least one filter adapted to the averaging length of the sensing head.

5. A magnetic device according to claim 4 wherein the filter comprises a digital filter.

6. A magnetic device according to claim 5 wherein the digital filter comprises a finite impulse response filter.

7. A magnetic device according to claim 2 wherein the digital signal processing unit comprises an integrator and a high pass filter to transform the leakage flux sensor signal into the trace that, added to the loss of metallic area signal, results in the high linear resolution metallic area measurement.

8. A magnetic testing device according to claim 1, wherein the object comprises a wire rope.

9. A magnetic testing device according to claim 1 wherein said means for increasing the linear resolution by processing the signal generated by the leakage flux sensor and the signal generated by the loss of metallic area sensor.

* * * * *

UNITED STATES PATENT AND TRADEMARK OFFICE
CERTIFICATE OF CORRECTION

PATENT NO. : 5,565,771
DATED : October 15, 1996
INVENTOR(S) : HAMELIN, et al.

It is certified that error appears in the above-identified patent and that said Letters Patent is hereby corrected as shown below:

ABSTRACT,

Line 18, "an" should read --any--.

Column 1

Line 65, "latter in" should read --latter into--.

Column 2

Line 6, "locate" should read --determine--;
Line 44, "Non Destructive" should read --Non-Destructive--;

UNITED STATES PATENT AND TRADEMARK OFFICE
CERTIFICATE OF CORRECTION

Page 2 of 2

PATENT NO. : 5,565,771
DATED : October 15, 1996
INVENTOR(S) : HAMELIN, et al.

It is certified that error appears in the above-identified patent and that said Letters Patent is hereby corrected as shown below:

Line 55, "however" should read --however,--.

Column 3

Line 9, "computerbased." should read --computer-based.--.

Column 4

Line 2, "coil based" should --coil based--;
    Line 7, "sensor based" should read --sensor-based--;
    Line 10, "coil based" should read --coil-based--;
Column 6, Line 12, "cross sectional" should read --cross-sectional--;
    Line 14, "and" should be deleted;
    Line 48, after "increasing" insert --increases--.

Signed and Sealed this

Ninth Day of December, 1997

Attest:

BRUCE LEHMAN

*Attesting Officer*     *Commissioner of Patents and Trademarks*